(12) United States Patent
Tubb

(10) Patent No.: US 11,017,891 B2
(45) Date of Patent: May 25, 2021

(54) TITRATION OF BASAL INSULIN WITH TWO MODES

(71) Applicant: SANOFI-AVENTIS DEUTSCHLAND GMBH, Frankfurt am Main (DE)

(72) Inventor: Andrew Tubb, Guildford (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 1151 days.

(21) Appl. No.: 15/324,997

(22) PCT Filed: Jul. 10, 2015

(86) PCT No.: PCT/EP2015/065883
§ 371 (c)(1),
(2) Date: Jan. 9, 2017

(87) PCT Pub. No.: WO2016/005586
PCT Pub. Date: Jan. 14, 2016

(65) Prior Publication Data
US 2017/0213009 A1    Jul. 27, 2017

(30) Foreign Application Priority Data

Jul. 11, 2014 (EP) .................................... 14176726

(51) Int. Cl.
*G16H 10/65* (2018.01)
*G16H 20/10* (2018.01)
*A61M 5/172* (2006.01)

(52) U.S. Cl.
CPC .......... *G16H 10/65* (2018.01); *A61M 5/1723* (2013.01); *G16H 20/10* (2018.01);
(Continued)

(58) Field of Classification Search
None
See application file for complete search history.

(56) References Cited

U.S. PATENT DOCUMENTS

2012/0116196 A1   5/2012   Tubb
2012/0232520 A1   9/2012   Sloan et al.

FOREIGN PATENT DOCUMENTS

CN    102369029    3/2012
CN    103813821    5/2014
(Continued)

OTHER PUBLICATIONS

Spencer, W. J.; "A Review of programmed Insulin Delivery Systems"; IEEE Transactions on biomedical Engineering, vol. BME-28, No. 3, Mar. 1981 (Year: 1981).*
(Continued)

*Primary Examiner* — Lori A. Clow
*Assistant Examiner* — Marie Archer
(74) *Attorney, Agent, or Firm* — Fish & Richardson P.C.

(57) ABSTRACT

A medical device data management unit includes a data storage and a processor. The data storage stores multiple measurement values of a physiological parameter of a user including a blood glucose level, multiple applied medicament dose values, time information associated with the multiple measurement values of the physiological parameter and one or more target ranges of the physiological parameter. The processor can determine a suggestion for a subsequent medicament dose value, check a prior suggestion and adjust the suggestion based on other measured values. The data management unit can be included in a medical device. The instructions to operate the data management unit can be encoded on a computer-readable medium.

12 Claims, 5 Drawing Sheets a)    b)    c)

(52) U.S. Cl.
CPC ..... *A61M 2205/50* (2013.01); *A61M 2205/52* (2013.01); *A61M 2230/201* (2013.01)

(56) References Cited

FOREIGN PATENT DOCUMENTS

| EP | 1281351 | 2/2003 |
|---|---|---|
| JP | H04-15035 | 1/1992 |
| JP | 2012-531950 | 12/2012 |
| WO | WO 2010/089304 | 8/2010 |
| WO | WO 2011/008520 | 1/2011 |
| WO | WO 2013/037754 | 3/2013 |

OTHER PUBLICATIONS

Dortch, M. J. et al; (2008). "A computerized insulin infusion titration protocol improves glucose control with less hypoglycemia compared to a manual titration protocol in a trauma intensive care unit". JPEN, Journal of Parenteral and Enteral Nutrition, 32(1), 18-27. (Year: 2008).*

Boord, J. B. et al; "Computer-based Insulin Infusion Protocol Improves Glycemia Control over Manual Protocol"; J. Am. Med Inform Assoc.; vol. 14; No. 3; May/Jun. 2007; p. 278-287. (Year: 2007).*

Kim, C. S. et al; "Insulin Dose Titration System in Diabetes Patients Using a Short Messaging Service automatically Produced by a Knowledge Matrix"; Diabetes Technology & Therapeutics; vol. 12; No. 8, 2010; p. 663-669. (Year: 2010).*

Dortch, M. J. et al; "A Computerized Insulin Infusion Titration Protocol Improves Glucose Control with less Hypoglycemia Compared to a Manual Titration Protocol in a Trauma Intensive Care Unit"; Journal of Parenteral and Enteral Nutrition; vol. 32; No. 1 (2007); p. 18-27. (Year: 2007).*

Arnolds et al.,"Common Standards of Basal Insulin Titration in T2DM," Journal of Diabetes Science and Technology, May 1, 2013, 77(3):771-778.

International Preliminary Report in International Application No. PCT/EP2015/065883, dated Jan. 17, 2017, 8 pages.

International Search Report and Written Opinion in International Application No. PCT/EP2015/065883, dated Feb. 18, 2016, 12 pages.

Inzucchi et al., "Management of hyperglycemia in type 2 diabetes: a patient-centered approach. Position statement of the American Diabetes Association (ADA) and the European Association for the Study of Diabetes (EASD)," Diabetologia; Clinical and Experimental Diabetes and Metabolism, Apr. 20, 2012, 55(6):1577-1596.

* cited by examiner

TITRATION OF BASAL INSULIN WITH TWO MODES

CROSS-REFERENCE TO RELATED APPLICATIONS

This application is a U.S. national stage application under 35 USC § 371 of International Application No. PCT/EP2015/065883, filed on Jul. 10, 2015, which claims priority to European Patent Application No. 14176726.9 filed on Jul. 11, 2014, the entire contents of which are incorporated herein by reference.

The present disclosure relates to a data management unit, a medical device, preferably a glucose meter, a method for operating a data management unit, a respective computer program and a computer program product.

The following description of the disclosure mainly refers to diabetes as a health problem and the blood glucose level as the physiological parameter to be controlled in order to assess the effectiveness of the prescribed treatment. However, the disclosure may also be used with regard to other health problems and for management of other physiological parameter data like (a) blood pressure in hypertensive heart disease, (b) cholesterol or lipoprotein profile in patients with risk factors for heart disease and stroke, (c) peak flow in asthmatic patients, or (d) coagulation in patients treated for hemophilia.

Diabetes mellitus is a group of metabolic diseases in which a person has high blood sugar, either because the pancreas does not produce enough insulin, or because cells do not respond to the insulin that is produced. The treatment of diabetes concentrates on keeping blood sugar levels as close to normal ("euglycemia") as possible, without causing hypoglycemia. This can usually be accomplished with diet, exercise, and use of appropriate medications (insulin in the case of type 1 diabetes; oral medications, as well as possibly insulin, in type 2 diabetes).

Essential elements of the management of diabetes with insulin are periodic checks of the glucose concentration in the blood performed by the patients themselves, in order to obtain regular information on the progress and success of the prescribed treatment. This understanding, and patient participation is vital, since the complications of diabetes are far less common and less severe in patients who have well-managed blood sugar levels. With regard to this it has to be considered that the blood glucose level fluctuates throughout the day and is directly influenced by the amount of insulin administered, as well as lifestyle factors such as the amount and kind of food that is consumed, the exercise level and stress.

Therefore, the monitoring of the sugar level in the blood with a data management unit serves a dual purpose: on the one hand it provides the patient with information about the current status of glycemic control. On the other hand can the measured values serve as information for the patient or a healthcare professional (HCP) to determine whether an adjustment in the medication, namely the amount of insulin to be taken, is indicated.

In order to achieve these goals or to get as close as possible to the desired glycemic control, it is common practice that blood glucose measurement (BGM) values are monitored by a data management unit or a blood glucose meter comprising such data management unit once or several times during the day, following a testing regime normally prescribed by an HCP. Additionally, some data management units provide suggestions for doses of the medicament to be administered or for dose changes for example based on the present blood glucose value and ingested carbohydrates.

A special role is played by the so-called fasting blood glucose measurement value (FBG). A fasting blood glucose measurement value is derived after several hours without eating (6 to 8 hours). The fasting blood glucose measurement value is typically taken in the morning before breakfast and is the most commonly performed test among insulin treated patients as it is used to assess the quality of the titration of long-acting basal insulin or analogs such as insulin glargine. The advantage of long-acting basal insulin or insulin glargine is that they have a duration of action of more than 24 hours or even more with a less peaked profile than NPH insulins. Thus, the profile more closely resembles the basal insulin secretion of the normal pancreatic β-cells.

For good or perfect glycemic control the dose of basal insulin or insulin glargine has to be adjusted for each individual in accordance with a blood glucose level to be achieved. Usually, the dose of insulin or insulin glargine is increased from an initial dose to a final dose over a certain time period until the specific blood glucose value, typically the fasting blood glucose (FBG) value, has reached the target range. In practice, such titration can be done by the health care professionals (HCPs). However, the patient may be empowered and trained by the HCPs to do their own titration. Such a self-titration can be supported by an intervention from a third party support or service or some intermediate combination.

In every day use, basal insulin or insulin glargine is typically under-dosed. Thus, there remains a gap between the initial dosing and an optimal dosing for achieving perfect or almost perfect glycemic control. This has a number of negative effects which better titration could help to eliminate. For example, if patients are not titrated, their blood sugar does not come down and as a result they do not feel better in the short term. Moreover, in the long term their HbA1c remains high and their health suffers. Thus, the patients may feel that their treatment is not working, and they may lose interest in the therapy or discontinue treatment.

Due to the almost peakless profile, basal insulin and insulin glargine are simple to titrate. Meanwhile, there is an array of approaches that physicians use for titration. Generally, these approaches suggest a specific dose adjustment within a specific time period until the target FBG is achieved. Each of these algorithms comes with specific rules, e.g. that the dose should not be increased if the blood glucose value (BG value) was below 70 mg/dl (low blood sugar) in the last week.

Document EP 1 281 351 A2 describes a diabetes management system which enables glycemic control for a subject. The described system includes an insulin delivery unit, a glucose sensor and a control unit. The control unit includes a processor unit that receives glucose value readings from the glucose sensor, executes an algorithm that predicts a glucose value at a predetermined time in the future, compares the predicted glucose value with the predetermined glucose value range, and determines a corrective amount of insulin to be administered when the predicted glucose value lies outside of the predetermined glucose value range. The glucose unit also includes a communication unit that transmits the corrective amount to the delivery unit.

In the document WO 2010/089304 A1 a medical device for providing information for glycemic control is described. The device comprises storage means arranged to store data, receiving means arranged to receive blood glucose value data and security data, data processing means arranged to execute a first processing function for modifying data retrieved from the storage means and to execute a second processing function for providing information for glycemic control based on the blood glucose value data and data retrieved from the storage means, validating means arranged to validate the received security data and to provide validation data corresponding to the validation of the received security data, and safety means arranged to control an execution of at least a predetermined function out of the first and second processing functions based on the validation data. The first processing function is a processing function for adjusting the profile parameters for a selected dose adjustment profile. The second processing function is a processing function for stepwise adapting a dose of insulin based at least on the selected dose adjustment profile and thereby determining the value for the dose of insulin to be set.

Although it seems that the titration of basal insulin and insulin glargine is simple for the patient (user) there is a risk for over-titration observed due to an occasional or short-term high blood glucose measurement value.

Hence, certain implementations of the subject matter of the present disclosure can be implemented to provide a data management unit, a medical device and a respective method which makes it safer for the user to avoid over-titration.

The above problem is solved by a data management unit with the features of claim 1.

In particular, the inventive data management unit comprises
   a data storage adapted to store
      a plurality of measurement values of a physiological parameter of a user, preferably a blood glucose level,
      a plurality of applied medicament dose values, each of which are preferably either measured or provided by the user,
      time information with regard to the plurality of measurement values of the physiological parameter and with regard to the medicament dose values comprising the time of measuring the physiological value and/or the time of application of the medicament dose values, and
      one or more target ranges of the physiological parameter,
   a processor adapted to
      determine a suggestion for a subsequent medicament dose value in a first mode or in a second mode, wherein at the beginning the medicament dose value determination is in said first mode,
      check prior determination of the suggestion for a subsequent dose value a first condition, whether the plurality of measurement values is below the upper end of the corresponding target range of the one or more target ranges over a predetermined period of time and/or over a predetermined number of recent measurement values using the time information of the plurality of measurement values, and switch from the first mode to the second mode, in case this first condition is true,
      wherein in the first mode the determination of a suggestion for a subsequent medicament dose value is based on at least one first predefined calculation rule using at least one recent measurement value of the physiological parameter and at least one recent applied medicament dose value,
      wherein in the second mode the suggestion for a subsequent medicament dose value is determined based on a second predefined calculation rule, wherein the suggestion for a subsequent medicament dose value is determined to be lower than or equal to an upper dose limit value based on at least one of the recently applied medicament dose values or
      based on a third predefined calculation rule considering a dose suggestion with a stable or decreased dose compared to one of the at least one of the recently applied medicament dose values.

The inventive data management unit provides the advantage, that as soon as the blood glucose measurement values, preferably the FBG, are consistently in or around target in the first mode (e.g. the mode in which full titration of the suggested dose is allowed), i.e. within a target range over a predetermined period of time (first condition), the processor enters a second mode, wherein the suggested medicament dose value will not be increased above the upper dose limit value even though some measurement values are outside target. In the second mode a slight decrease of medicament dose value is possible. Alternatively, in the second mode no dose limit value is defined but compared to the first mode an at least one calculation rule allowing or considering a dose increase is basically switched off and therefore cannot be used. Hence, an at least one third calculation rule allowing or considering a dose decrease or stable dose (which may be preferably similar to at least one corresponding calculation rule of the first mode) is applied in the second mode. That means that in this case either no dose suggestion can be given or the given dose suggestion is equal to or less than one of the recently applied dose values or suggested doses. Therein, the recently applied dose values/suggested dose are the last applied dose value/suggested dose or a mean value of a predefined number of recently applied dose values/suggested doses or of recently applied dose values/suggested doses over a predefined time period.

Further, the upper dose limit value is defined as the suggested dose value of the previous suggestion for a medicament dose, or a mean value of a predefined number of previous suggested doses or one of both values plus a predefined additional dose value, for example two units. Further, the upper dose limit value may be reduced in the second mode accordingly, in case a subsequent suggested dose value in the second mode is lower than a previous suggestion for a medicament dose used for determination of the actual upper dose limit value.

In the first mode the user (patient) adjusts the suggested medicament dose value using the at least one first predefined calculation rule with the goal that the measurement value of the physiological parameter reaches target range and stays continuously there. Therein, with regard to diabetes the blood glucose measurement value is titrated to reach a target range which is between, for example 90 mg/dl and 130 mg/dl.

As mentioned above, in the first condition it is checked, whether the plurality of measurement values is below the upper end of the corresponding target range of the one or more target ranges over a predetermined period of time and/or over a predetermined number of recent measurement values using the time information of the plurality of measurement values. This includes the case that it is checked whether a minimum number of measurement values is below the upper end of the corresponding target range of the one or more target ranges or that it is checked whether a minimum number of measurement values from a predetermined range of minimum and maximum numbers of measurement values are below the upper end of the corresponding target range of the one or more target ranges, wherein the measurement values are gathered within a maximum timeframe, wherein the number of measurement values is limited to a maximum amount per time period, e.g. one day, is below the upper end of the corresponding target range of the one or more target ranges.

Similarly, if the processor is currently in the second mode, it is checked prior determination of the suggestion for a subsequent dose value a second condition, whether the plurality of measurement values is above the upper or below the lower end of the corresponding target range of the one or more target ranges over a predetermined period of time or over a predetermined number of recent measurement values using the time information of the plurality of measurement values, and switch from the second mode to the first mode, in case this second condition is true.

In the present disclosure the term "medicament dose value" refers to an absolute medicament dose value, for example units of long-acting insulin. Hence this term also includes the medicament dose change accordingly, if one takes the preceding medicament dose value into account. It is simple to determine the medicament dose change by subtraction of the preceding (absolute) medicament dose value from the suggestion for a subsequent (absolute) medicament dose value. The suggestion for a subsequent medicament dose value is a dose value which is suggested to the user as the next medicament dose value. The user may or may not apply the suggested dose e.g. by injection.

The time information with regard to the plurality of measurement values of the physiological parameter and with regard to the medicament dose values may comprise the time of measuring the physiological value and/or the time of application of the medicament dose values. It may be realized by the time stamp associated to each measurement value comprising date and time information of a certain time point during the measurement process resulting in the respective measurement value, for example the completion of the measurement process or receipt of the new measurement value by the data management unit. Usually the time stamp is associated by the measurement unit and is transferred to the data management unit with the respective measurement value. In case the new measurement value is not associated with a respective time stamp by the measurement unit, the time stamp is assigned by the processor after receipt of the measurement value. The time information of the medicament dose value may be the time stamp comprising date and time information of the determination of the medicament dose value (in case the user has acknowledged to apply the suggested medicament dose immediately) or the time information comprising date and time provided by the user with regard to the respective medicament dose value as application time.

In a preferred embodiment the measurement values of a physiological parameter comprise in particular the FBG value or values.

In a preferred embodiment the processor is adapted to execute the second calculation rule wherein at first an intermediary result for the suggestion for the subsequent medicament dose value based on the at least one first predefined calculation rule using at least one recent measurement value of the physiological parameter and at least one recently applied medicament dose value is determined, then the intermediary result with the upper dose limit value is compared, thereafter the suggestion for the subsequent medicament dose value is determined being the upper dose limit value in case the intermediary result is greater than or equal the upper dose limit value, or otherwise being the intermediary result or a value between the intermediary result and the upper dose limit value calculated by a third predetermined calculation rule.

For example, by the third calculation rule the suggestion for the subsequent medicament dose value is calculated being the arithmetic mean of the intermediary result and the upper dose limit value.

In another embodiment the processor is further adapted to determine the suggestion for the subsequent medicament dose value by the at least one first predefined calculation rule additionally based on further information about a further physiological parameter and/or an event with regard to the user. Therein, the event with regard to the user may be represented by an event tag. Preferably, the event tag for blood glucose measurement values comprises the event nil (no-tag) and in particular at least one of the following group of events comprising fasting, pre-meal, post-meal, pre-meal breakfast, post-meal breakfast, pre-meal lunch, post-meal lunch, pre-meal supper, post-meal supper, night time and exercise.

In a preferred embodiment a tag is automatically selected and only needs to be confirmed by the user, thus the inventive data management unit reduces the number of steps for tag selection.

In an alternative embodiment the processor is adapted to automatically select the tag of one of the at least one meal event or the fasting tag after one of the tags "before meal" or "after meal" was selected by the user. In this embodiment the data storage comprises the time ranges for tagging preselection of the meals, only, for example "breakfast", "lunch" and "dinner". Preferably, the "fasting" time range for tagging preselection is also provided. This embodiment also supports the user during tagging and reduces the risk of erroneous tagging.

Further information about a physiological parameter may be the amount of user's food intake and kind of food or the heart rate. Alternatively or additionally the processor is further adapted to receive a data input related to the physiological parameter, wherein the data input comprises at least one of the following physiological parameters:

occurrence or number of hypoglycemic events after a predetermined point in time, e.g. the last use of the data management unit by the user, the time information of the previous measurement value or time information of the previously determined medicament dose value, occurrence or number of hyperglycemic events after a predetermined point in time, e.g. the last use of the data management unit by the user, the time information of the previous measurement value or time information of the previously determined medicament dose value.

The above problem is also solved by a medical device comprising the above explained data management unit with the same advantages.

For the same reason the above problem is also solved by a method for operating a data management unit with a data storage comprising one or more target ranges of a physiological parameter and a processor, wherein the method comprises the following steps:

determining a suggestion for a subsequent medicament dose value in a first mode or in a second mode, wherein at the beginning the medicament dose value determination is in said first mode, checking prior determination of the suggestion for a subsequent dose value a first condition, whether a plurality of measurement values stored in the data storage is below the upper end of the corresponding target range of the one or more target ranges over a predetermined period of time and/or over a predetermined number of recent measurement values using a time information of the plurality of measurement values, and switching from the first mode to the second mode, in case this first condition is true, wherein in the first mode the determination of the suggestion for a subsequent medicament dose value is based on at least one first predefined calculation rule using at least one recent measurement value of the physiological parameter and at least one recent applied medicament dose value, wherein in the second mode the suggestion for a subsequent medicament dose value is determined based on a second predefined calculation rule, wherein the suggestion for a subsequent medicament dose value is determined to be lower than or equal to an upper dose limit value based on at least one of the recently applied medicament dose values or based on a third predefined calculation rule considering a dose suggestion with a stable or decreased dose compared to one of the at least one of the recently applied medicament dose values.

The embodiments of the inventive method and their advantages are already explained above with regard to the data management unit. It is therefore referred to the description of the data management unit concerning the embodiments of the inventive method.

With the same advantages as explained above the problem is solved by a computer program for operating a data management unit with a data storage comprising one or more target ranges of a physiological parameter and a processor, wherein the computer program comprises:

code for determining a suggestion for a subsequent medicament dose value in a first mode or in a second mode, wherein at the beginning the medicament dose value determination is in said first mode, code for checking prior determination of the suggestion for a subsequent dose value a first condition, whether the plurality of measurement values is below the upper end of the corresponding target range of the one or more target ranges over a predetermined period of time and/or over a predetermined number of recent measurement values using the time information of the plurality of measurement values, and switch from the first mode to the second mode, in case this first condition is true, wherein in the first mode the determination of the suggestion for a subsequent medicament dose value is based on at least one first predefined calculation rule using at least one recent measurement value of the physiological parameter and at least one recent applied medicament dose value, wherein in the second mode the suggestion for a subsequent medicament dose value is determined based on a second predefined calculation rule, wherein the suggestion for a subsequent medicament dose value is determined to be lower than or equal to an upper dose limit value based on one of the recently applied medicament dose values or based on a third predefined calculation rule considering a dose suggestion with a stable or decreased dose compared to one of the at least one of the recently applied medicament dose values.

The above computer program may be realized with the embodiments as mentioned above with regard to the above inventive method for operating a medical device.

The above problem is further solved by computer program product comprising a computer-readable medium bearing computer program code embodied therein for use with a computer, wherein the computer program code comprises the above mentioned computer program.

The above-mentioned advantages as well as other advantages of various aspects of the present disclosure will become apparent to those of ordinary skill in the art by reading the following detailed description with the explanation of the accompanying drawings. All features described above and below and/or illustrated per se or in any combination form the subject-matter of the disclosure, independent of their inclusion in the claims or their back-reference.

Exemplary embodiments of the present disclosure are described herein with reference to schematic drawings, in which FIG. 1 shows the medical device according to a preferred embodiment of the disclosure in a perspective view;

FIG. 2 shows a diagram of the medical device as shown in FIG. 1;

FIG. 3 presents an example of the display of the medical device as shown in FIG. 1 in a "Logbook" route;

The following paragraphs will describe various embodiments of the disclosure. For exemplary purpose only, the embodiments are outlined in relation to a medical device with regard to blood glucose level measurement. However, the used terminology and the description of the embodiments with respect to the medical device or the method are not intended to limit the principles and ideas of the invention to such a single device or method and may be adapted to other physiological values accordingly.

Figure 1:
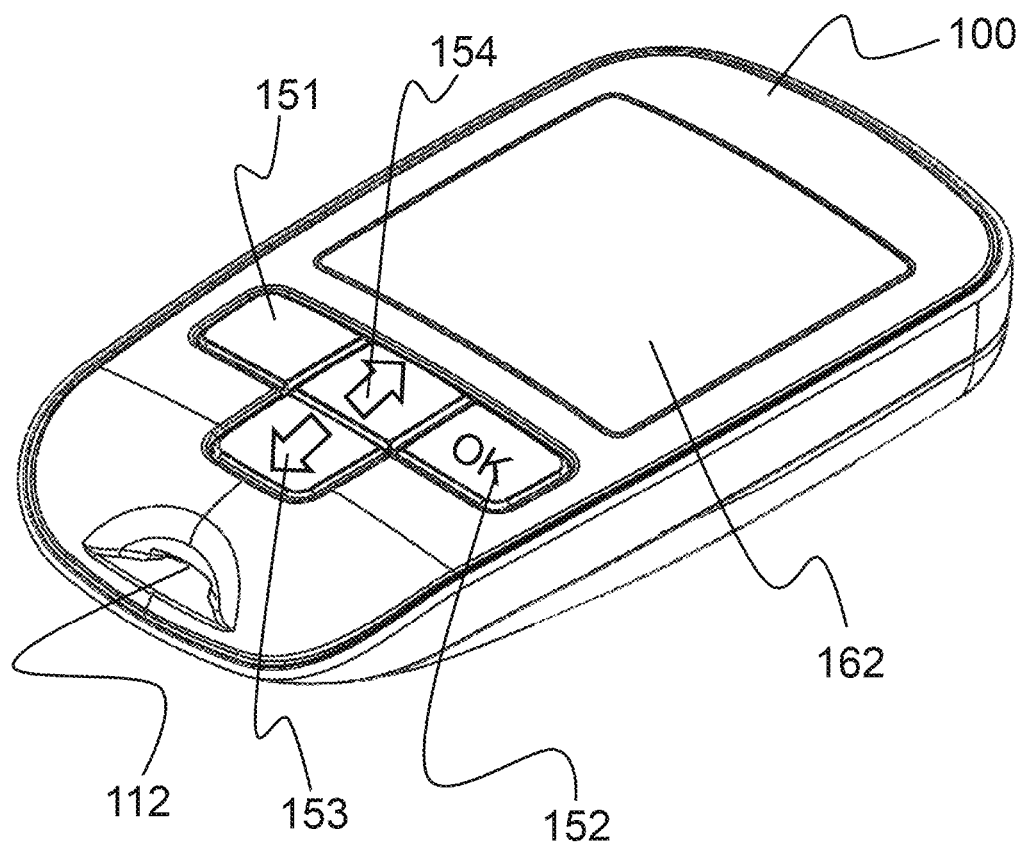
Figure 2:
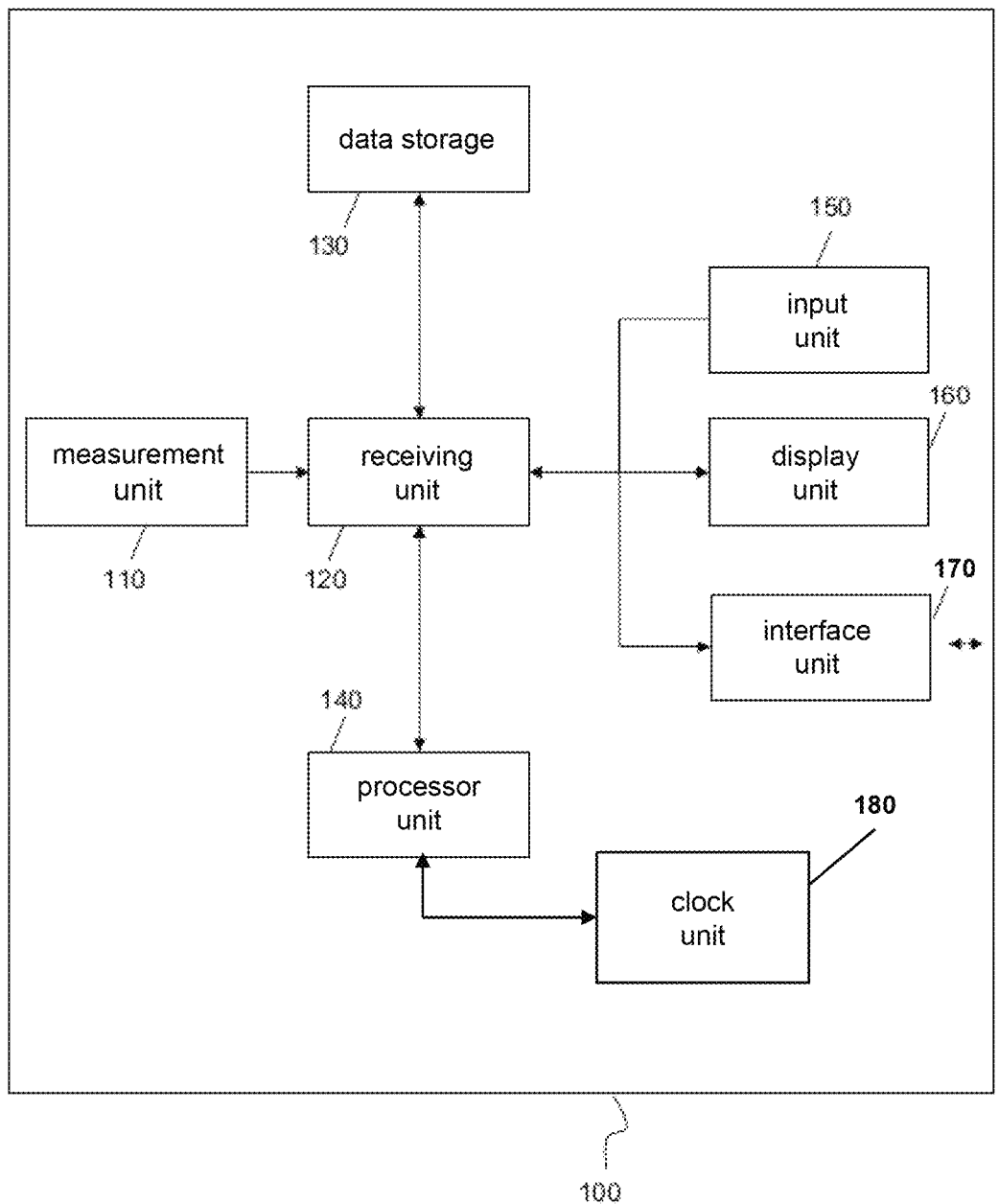

FIG. 1 is a schematic drawing and FIG. 2 is a schematic diagram of a medical device 100 according to a preferred embodiment of the disclosure. Preferably, the medical device 100 comprises a blood glucose measurement unit 110, which is arranged to measure the blood glucose level. Further, the measurement unit 110 comprises an interface and a slot 112 for inserting a test strip.

The blood glucose measurement unit 110 is connected to a receiving unit 120, which is arranged to forward e.g. blood glucose measurement data received from blood glucose measurement unit 110 to a data storage 130 (storage unit or means) or memory, such as a Flash memory. Alternatively, the receiving unit 120 may retrieve stored data such as e.g. blood glucose value data from the storage 130 and forward it to a processor 140 (processing unit or means), such as a microcontroller or microprocessor, a digital signal processor, and/or the like. Alternatively, the receiving unit 120 directly forwards the blood glucose value data received from the blood glucose measurement unit 110 to the processor 140.

Receiving unit 120 is further connected to a user input unit 150 of a user interface. The user input unit 150 is arranged to receive input from the user of the medical device 100 for example by key 151, confirmation key (OK button) 152, key 153 for scrolling down (downward button) and key 154 for scrolling up (upward button). The user input data are forwarded from the user input unit 150 to the receiving unit 120, which either forwards it to the processor 140 or to the data storage 130.

Furthermore, the user interface of medical device 100 comprises a display unit 160 with a display 162, which is connected to the receiving unit 120 as well. Preferably, the display unit 160 receives data to be displayed by the display 162 from the receiving unit 120 or the processor 140.

Preferably, the medical device 100 additionally comprises a further interface 170, for example a wired interface such as a serial port, a Universal Serial Bus (USB) interface, a mini-USB interface, or a wireless interface such as an infrared (e.g. an IRDA) interface, a Bluetooth™ interface, and/or the like, in order to receive data and/or to transmit data. The interface 170 is preferably connected to the receiving unit 120 in order to receive data from the receiving unit 120 and/or to forward data to the receiving unit 120.

Additionally, the medical device 100 comprises a clock unit 180 which provides a date and time information, preferably based on a clock generator, which may be displayed at the display 162. Further, the clock unit 180 provides date and time information in particular for generating a time stamp for an associated blood glucose measurement or medicament dose value.

As outlined above, the medical device 100 preferably comprises a blood glucose measurement unit 110. The blood glucose measurement unit 110 is arranged to measure the blood glucose level in the blood of e.g. the user by testing a drop of blood on a test strip that is inserted into the slot 112. The measurement may be conducted using e.g. an electrochemical method. Full insertion of the test strip in the slot 112 may be detected by a respective sensor. The measured blood glucose value is transformed to blood glucose value data and forwarded preferably immediately or on demand to the receiving unit 120. Alternatively, the blood glucose measurement unit 110 is arranged to measure the blood glucose level of the user via infrared diagnosis or an alternative contactless measurement method.

According to a further alternative (not depicted in FIG. 1) the blood glucose measurement unit 110 is implanted in the body of the user of the medical device and forwards the data to the receiving unit 120 either via a wired connection or via a wireless connection. In an embodiment, such an implanted blood glucose measurement unit 110 is a continuous measurement sensor e.g. based on a chip which may allow a continuous closed loop control. In the latter case the medical device comprises two parts, one part contains the measurement unit 110 and the other part the remaining units of the medical device. The blood glucose measurement unit 110 preferably forwards the blood glucose measurement value data to the receiving unit 120 via interface 170. According to a further alternative the medical device does not comprise a blood glucose measurement unit which measures the blood glucose values, but receives blood glucose value data from an external unit.

The measurement of the blood glucose measurement is preferably triggered by the receiving unit 120 which sends a respective signal to the blood glucose measurement unit 110. According to one preferred alternative the receiving unit 120 receives a trigger signal generated by user input which is received via user input unit 150 or based on a signal from the slot 112 detecting a test strip. Alternatively, the trigger signal is generated automatically by the clock unit 180 or by the processor 140.

Preferably, the receiving unit 120 is represented e.g. by the input ports and output ports of a microprocessor or a bus system managing the data handling between several functional units. This includes bus systems, such as e.g. Advanced Microprocessor Bus Architecture bus systems implemented in a microprocessor or external bus systems connected to a microprocessor. Via the receiving unit 120, data are retrieved from the data storage 130 on demand and forwarded to the processor 140, to the display unit 160 or to the interface 170. Moreover, the receiving unit 120 forwards control signals, such as trigger signals or control signals e.g. to the blood glucose measurement unit 110, the display unit 160 or the interface 170.

The data storage 130 is arranged to store data entered via the user input unit 150, a plurality of blood glucose measurement data received from the blood glucose measurement unit 110 together with the time stamp and/or at least one event tag associated to each measurement data, a plurality of applied medicament dose values, for example provided by the user via the user input unit 150 or measured by a dosing device and provided via interface 170, data calculated from the plurality of blood glucose measurement values processed by the processor 140 and/or data received via interface 170. Additionally, the data storage is arranged to store data like medicament dose values determined by the processor 140 and confirmed by the user, for example using the confirmation key 152, as the medicament dose value actually applied.

Furthermore, data storage 130 is arranged to provide the stored data to the processor 140, to the display unit 160 and/or to the interface 170. The data storage 130 is preferably implemented as a semiconductor memory such as a Flash memory. Alternatively, it is implemented as a hard disk memory or an on-chip memory of the processor 140.

The processor 140 is preferably a microprocessor or any other functional unit capable of processing data.

The user input unit 150 is preferably implemented as a keyboard comprising one or more push buttons 151, 152, 153, 154. The keyboard may comprise one or more soft keys, wherein the function of the soft keys may be displayed on the display 162. Alternatively, the user input unit 150 is a key board or a touch screen. Alternatively, the user input unit 150 comprises a microphone for receiving speech input so that data can be entered via speech input.

After facilitating a blood glucose measurement a tag may be automatically associated to the measurement value referring to lifestyle data. The automatically selected tag may be changed by pressing the up or down keys 153, 154 scrolling upwards or downwards through the different tags which are for example the fasting tag, pre-meal tag, post-meal tag and no-tag, respectively, referring to a measurement value which is a fasting blood glucose value, a pre-meal blood glucose value, a post-meal blood glucose value and a blood glucose value that cannot be associated to one of the previous lifestyle parameter.

The display unit 160 preferably comprises an LCD or LED display 162. Preferably, the display displays a number of alphanumerical characters so that e.g. the presently measured blood glucose value can be displayed together with additional instructions for the user. Alternatively or additionally, the display unit 160 comprises a graphic display in order to display graphs or graphics such as icons. Further the display of the display unit 160 may comprise a touchscreen.

The interface 170 is preferably a wireless interface, such as IRDA, Bluetooth™, GSM, UMTS, ZigBee, or WI-FI, etc.

Alternatively, the interface is a wired interface, such as a USB port, mini-USB port, serial data port, parallel data port, etc., for receiving and transmitting data. In a further alternative embodiment the medical device 100 does not comprise an interface 170.

According to another alternative embodiment, medical device 100 comprises a memory card reader or a memory card reader interface. The memory card reader is preferably adapted to read information from a memory card, such as a Flash memory card, or any type of SIM card. For this purpose, the memory card comprises a memory, wherein at least one of a selected algorithm together with corresponding parameters, a history of the blood glucose values and/or insulin doses administered, etc. is stored. Thus, in the case that the medical device 100 has a defect, the relevant data may still be stored on the memory card which can be easily removed from the memory card reader of the medical device 100 and transferred to a new medical device 100. Moreover, the memory card 100 may be used in order to provide information on the history of the treatment to e.g. an HCP.

In the case that the memory card is a SIM card providing subscriber identification for a mobile communication network and the interface unit 170 is additionally a mobile communication interface, additional functions of the medical device 100 can be unlocked by the provider of the SIM card via a telecommunication channel. This offers the possibility that the medical device 100 can communicate with other telecommunication devices via predefined channels, such as UMTS or GSM. Via the international mobile subscriber identity, also called IMSI, stored in the SIM card, the medical device 100 identifies itself within the network and, thus, can be addressed via the network. In such a case the medical device 100 can be easily checked, remote controlled, updated, monitored, etc., via interface unit 170, e.g. by addressing the mobile communication unit with a phone number.

Furthermore, the medical device 100 is able to transmit data via SMS, e-mail or via mobile internet connection. Moreover, this offers the possibility to locate the medical device 100 in an emergency case.

In the case that the blood glucose measurement unit 110 is a sensor which is e.g. implanted a dose delivery unit with an insulin pump or a pump for another medicament forming an automatic delivery system may be additionally provided. This delivery system may determine the applied medicament dose and provide the dose together with the respective application time stamp via the interface 170 to the data storage 130.

Figure 5:
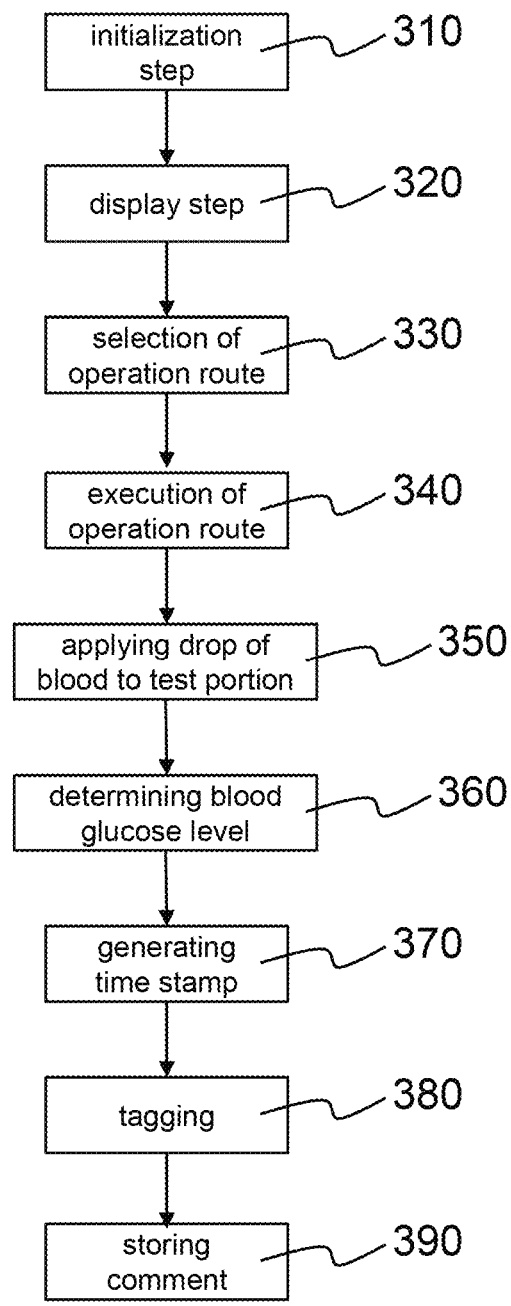
FIG. 5 illustrates the functioning of the inventive medical device, in particular in the "Measure BG" route by a respective flow diagram

As shown in FIG. 5, the processor 140 of the medical device 100 is capable to perform a number of process steps. According to one embodiment after switching on, e.g. by pressing a key 151, 152, 153 or 154, preferably the confirmation key 152 for a predetermined time, or detection of a test strip within the slot 112, the medical device 100 performs initialization step 310 for initializing the functional components of the medical device 100. After this, the different operation routes which are implemented in the medical device 100, are displayed in the display step 320, preferably operation routes such as "Measure BG", "Logbook", "Settings" and/or "Titration".

In step 330 the user selects one of the displayed operation routes via the user input unit 150, for example by means of the keys 153, 154 for scrolling down or up, and confirms the selection of the route using the confirmation key 152. Alternatively, there may be provided a separate key for one or more of the operation routes, for example a key for the "Titration" route, also called the "Dose helper key".

In step 340 the selected operation route is executed. As an example the route "Measure BG" is selected for executing a blood glucose measurement. Upon execution of this route the user/user is requested to provide a test strip with a blood sample.

In the "Logbook" route the history of previous measurements and statistical results may be calculated and displayed. The "Settings" route allows the user to define and change some parameters of the medical device 100, e.g. time ranges for tagging preselection for a number of pre-set events. In the "Titration" route a dose suggestion may be provided by the medical device 10 for basal insulin or analogue in a first mode or in a second mode.

After selecting the route "Measure BG", in step 350 a drop of blood is applied to the test portion of the test strip which is inserted in slot 112 of the medical device 100.

According to an alternative version of the operation process steps 310 to 340 may be skipped in the case that a specific operation route is preselected. In this case, after initialization, the preselected operation route, which is either preselected by the user or automatically selected in accordance with a specific event, for example the detection of a fully inserted test strip in slot 112, the operating process proceeds with the following step 350 and asks the user to apply a drop of blood.

Now in step 360 the measurement unit 110 determines e.g. by an electrochemical or an optical method the blood glucose level and displays the respective new measurement value at the display 162.

In the next step 370 the clock unit 180 generates a time stamp of the present measurement comprising a date and time information. The time stamp is also displayed in display 162 and both, the present blood glucose measurement value and the associated time stamp is transferred by receiving unit 120 to the data storage 130.

Figure 4:
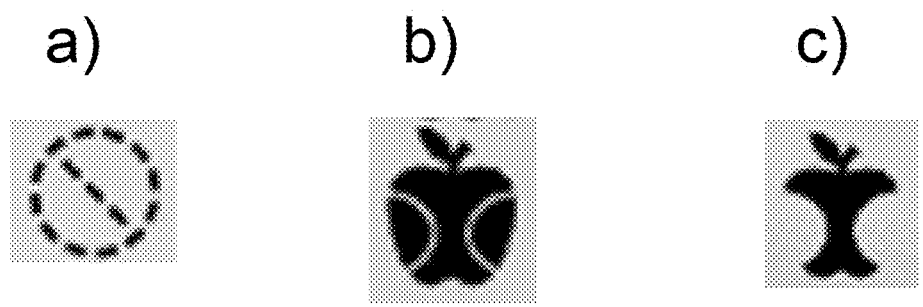
FIG. 4 illustrates further examples of tag signs as they are displayed on a display of the medical device as shown in FIG. 1.

In the next step 380 the user selects one of the event tags "pre-meal" and "post-meal" represented by a full apple as shown in FIG. 4b) in case of the pre-meal tag and represented by a bitten apple as shown in FIG. 4c) in case of the post-meal tag and confirms the tag. Then, the processor 140 may automatically select the associated meal according to the above time range for meal times according to the time information of the time stamp, preferably without further user confirmation. For example, the processor selects "supper" if the time information of the present time stamp is 7:35 p.m. Accordingly the tag comprises the information "pre-meal" or "post-meal" and "supper" and forms a composite tag which is then stored in the data storage 130 initiated by the processor 140.

In order to show that a confirmation is necessary the tag sign 168 displayed on display 162 is blinking/flashing. Now, the user may confirm the fasting tag for example by pressing the confirmation key 152. Alternatively, the user may change the tag using the up and down keys 153, 154 into the pre-meal tag, the post-meal tag or the no-tag (nil). If the correct tag is chosen the user confirms the tag by pressing the confirmation key 152. By confirmation of the tag with the confirmation key 152 the flashing of the displayed tag sign is stopped and the tag sign is displayed continuously without blinking. In this state, pressing the up/down keys 153, 154 will not change the tag. Then, the processor 140 initiates storage of the associated, confirmed tag with regard to the recent measurement value in the data storage 130 via receiving unit 120.

In the next optional step 390 a comment to the present measurement value may be selected by the user using the up and down keys 153, 154. The comment may then be confirmed with the confirmation key 152, wherein the chosen comment is then stored in the data storage 130 associated to the present measurement value as well.

Alternatively or additionally, the user may be asked in step 390 whether there are hypoglycemic events (hypos) are occurred and, if yes, which number, and/or whether there are hyperglycemic events (hyper) are occurred and, if yes, which number, since last measurement or last use of the medical device 100. Alternatively or additionally the user has to provide the information about the injected medicament dose value after a predetermined point in time, e.g. last use of the medical device or the time stamp of the last (previous) measurement value, wherein preferably the injected medicament dose value is automatically selected as the dose of the last (previous) suggested dose by a titration method.

When the medical device 100 is in the "Measure BG" route, the device may turn into the sleep state (step 400) automatically after for example 120 seconds without any new action. Once the device has returned a new measurement value, the device turns to the sleep state automatically after for example 60 seconds without any user interaction.

Figure 3:
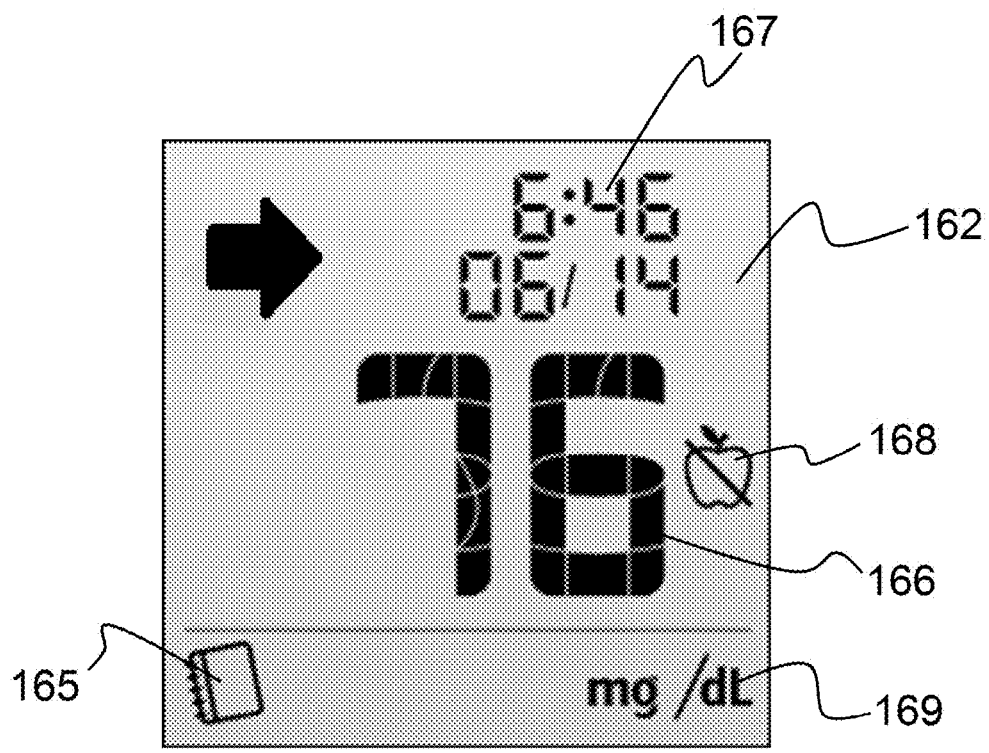

As explained above the medical device 100 provides at least one memory review mode which is called "Logbook" route. The "Logbook" route is entered when the user activates the medical device 100 by pressing e.g. the confirmation button 152. Then a display as depicted in FIG. 3 is shown with a measurement value. Therein, the user knows from the "Book" sign 165 in the lower left corner of the display that he/she has entered the "Logbook" route.

In the "Logbook" route the measurement values are preferably displayed in the order in which the entries are entered into the device, or alternatively according to the time and date assigned to the measurement values. In particular the most recent blood glucose measurement value is shown upon entry into the "Logbook" route. Pressing the up and down keys 153, 154 the user may scroll through the records, for example by pressing the down key 153 the user may scroll backwards in time and by pressing the up key 154 the user scrolls forward in time.

The display 162 in the "Logbook" route further shows the blood glucose measurement value 166 as biggest number in the center of the screen. Above the measurement value 166 the associated time stamp 167 including date and time is displayed. On the right side the associated tag as a sign 168 is provided, wherein the sign may show for example an empty, struck out apple as shown in FIG. 3 in case of an associated fasting tag, a full apple as shown in FIG. 4b) in case of an associated pre-meal tag, a bitten apple as shown in FIG. 4c) in case of an associated post-meal tag or a struck out circle as shown in FIG. 4a) in case of an associated no-tag. Additionally, in the lower right corner of the display 162 the measurement unit 169 for the blood glucose value is provided.

Figure 6:
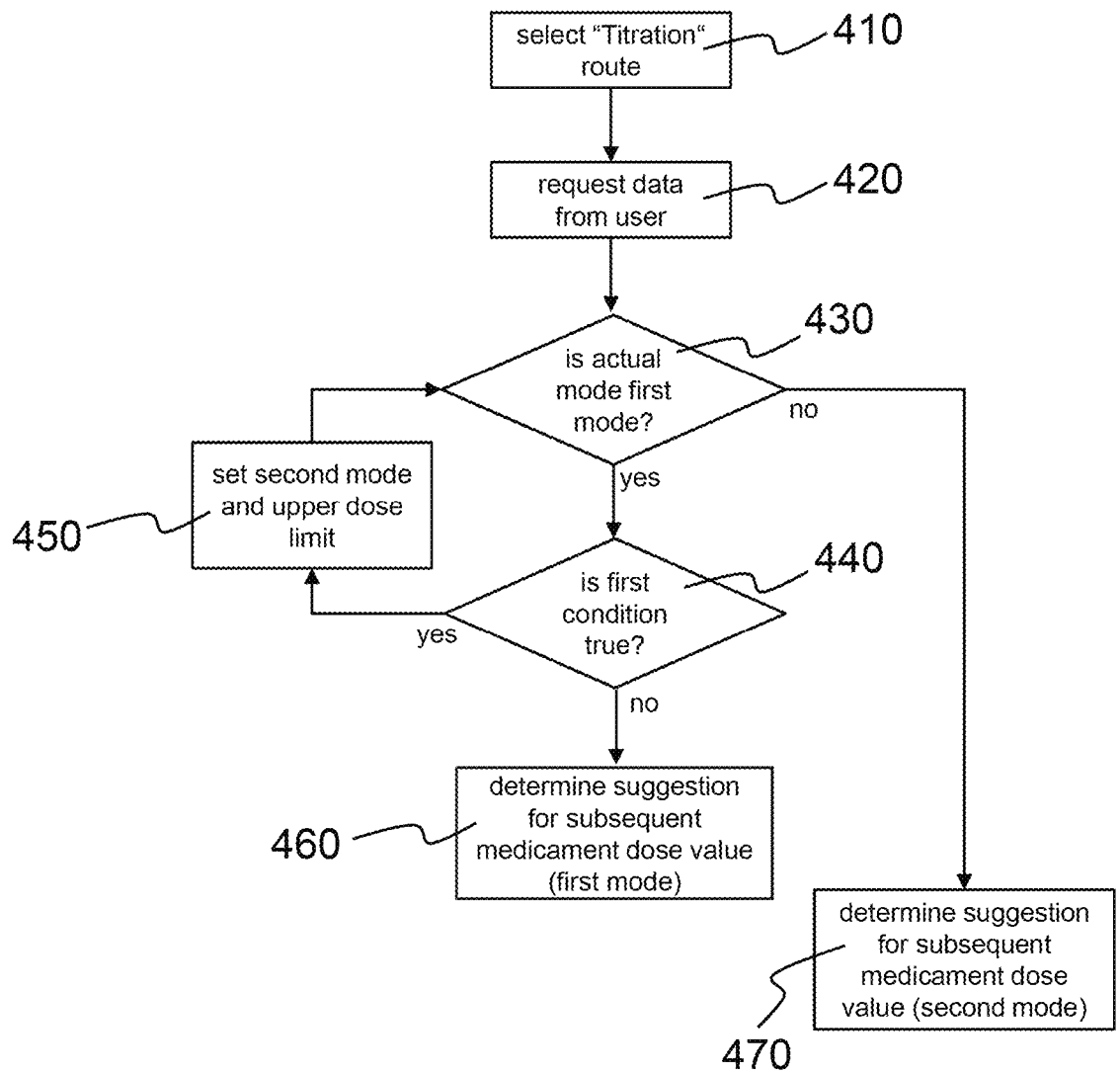
FIG. 6 shows a flow diagram comprising the inventive method realized by the inventive medical device in the "Titration" route.

In the "Titration" or "Dose Helper" route the user is provided with a dose suggestion preferably for basal insulin or analog if some of predefined conditions are fulfilled in a first mode (full titration) or in a second mode (partly titration). The method used in this route is based on at least the most recent fasting glucose value and other information like number of hypers and hypos and/or previous doses. The process steps executed by the processor 140 in the "Titration" route are depicted in FIG. 6.

At first, in step 410 the user selects the "Titration" route by scrolling with the up and down keys 153, 154 in the operations menu and confirms this route by pressing the confirmation key 152.

In the next step 420 of this route the user may be asked, in case there are two fasting measurement values within one single day tagged with the fasting tag, which fasting blood glucose measurement value has to be used for the titration algorithm. Further in this step, additional data are requested from the user, if necessary or not known yet, like occurrence or number of hypoglycemic events after a predetermined point in time, e.g. the last use of the data management unit by the user, the time information of the previous measurement value or time information of the previously determined medicament dose value, occurrence or number of hyperglycemic events after a predetermined point in time, e.g. the last use of the data management unit by the user, the time information of the previous measurement value or time information of the previously determined medicament dose value, and/or injected medicament dose value at a certain point in time, e.g. the last use of the medical device or the time stamp of the last (previous) measurement value, wherein preferably the injected medicament dose is automatically selected as the dose of the last (previous) suggested dose.

Additionally, in step 420 it may be checked whether the current time is within a predefined time interval from the last known dose or the last dose is entered with a time less than the predefined time interval, preferably 18 hours, from the current time. In this case, the following process steps may be skipped and the display of display unit 160 may show the message that dose helper is unavailable because it is too close to the last insulin dose, or the dose helper may ask another question regarding the time of the last dose. In this embodiment it is assumed that the dose helper functionality is only used in close temporal proximity of dose administration.

In another embodiment, for dose administration a certain time or time range of day may be predefined. For example, usual dose time may be 7 p.m. and the usual dose time range between 4 p.m. and 10 p.m. In this case, another check whether the current time is between 4 p.m. and 10 p.m. may be performed during step 420. If the current time is outside this range, again, step 420 may be skipped and the display of display unit 160 may show the message that dose helper is unavailable because it can only be run at the usual dose time.

Now, the processor checks in step 430, whether the actual mode is the first mode, where the medicament dose value is fully adjusted, for example using a first mode flag which is zero in the first mode. During first execution of the process of FIG. 6 the first mode flag is set to zero indicating the first mode.

Afterwards, in step 440, in case the actual mode is the first mode, a first condition is checked, whether the FBG values over a predetermined period of time and/or over a predetermined number of recent measurement values (e.g. last 30 days, minimum 15 FBG values within the last 30 days) are within the target range. If this is the case (yes), the processor changes in step 450 the first mode flag from zero to one indicating that "Titration" route is now in the second mode as the FBG value seem to be stabilized. Further, the actual medicament dose value (the one which was applied most recently) is chosen as the upper dose limit value. Alternatively, the upper dose limit value may be determined, for example, as the arithmetic mean of the applied medicament dose values of the last 5 days or the last 30 days. Then, the process will continue with step 430.

In case the first condition of step 440 is answered with "no" the process executed by processor 140 continues in the first mode and with step 460 determining using at least one first predefined calculation rule whether the actual medicament dose value must be changed and provides the user with a suggestion for a subsequent medicament dose value or the information that the medicament dose does not have to be changed or the information that a suggestion for a subsequent medicament dose value cannot be determined because, for example, more information (e.g. more recent FBG values or previous medicament dose values and their time information) is needed.

The dose suggestion is determined by the processor 140 preferably based on previous fasting FBG values and/or other measured blood glucose values, previous administered insulin doses and other lifestyle information like hypoglycemia symptoms or low blood sugar values. Additionally, exercise information, nutrition facts and additional fast-acting insulin doses as well as stress information may be considered. In particular, it is determined whether a single value of FBG or a mean value FBG of, for example at least three days within a five day period, is within a target blood glucose range which was previously defined for the certain user. If the single or mean FBG value is above the target range, usually a dose increase is suggested, if the single or mean FBG value is below the target range, a dose decrease may be suggested.

For example, the following calculation rules may be used in the first mode, wherein the target range is e.g. 90 mg/dl (lower limit) to 130 mg/dl (upper limit). If the median FBG value for last A days (at least B FBG values minimum necessary) is above the predefined FBG target range upper limit, increase the medicament (long acting insulin) dose value by X units every Y days (for example A=5, B=3, X=2, Y=3). Further, if at least C FBG values for last D days is less than a FBG target lower limit, decrease the medicament dose value by the greater of Z1 units or Z2% of the previous dose (for example C=2, D=3, Z1=2, Z2=5). If there are any low blood glucose measurement values lower than 70 mg/dl or any hypo symptoms decrease the medicament dose value by greater of E units or F % of the previous dose (for example E=4, F=10).

The screen of display unit 160 in step 460 may provide the possibility that the suggested insulin dose is confirmed and saved in case the user immediately administers the suggested dose. In this case the suggested and administered dose is saved in storage unit 130. Alternatively, the user may change the suggested dose and save it after administration.

In case that in step 430 the first mode flag is not zero but one the process is in the second mode, where the medicament dose value is only partly adapted, and continues with step 470 where a suggestion for a subsequent medicament dose value is determined based on at least one second predefined calculation rule. Therein, for example, if the median FBG value for last A days (at least B FBG values minimum necessary) is above the predefined FBG target range upper limit, an intermediary result for the suggestion for a subsequent medicament dose value is determined by the preceding medicament dose value increased by the medicament dose value by X units every Y days (for example A=30, B=15, X=2, Y=15). In case the intermediary result is greater than the upper dose limit value the preceding medicament dose value is not changed so that the suggestion for a subsequent medicament dose value is equal to the preceding medicament dose value. In case the intermediary result is equal to or less than the upper dose limit value the suggestion for a subsequent medicament dose value is determined as the intermediary result. Alternatively, the rule determining that the preceding medicament dose value is increased by the medicament dose value by X units every Y days is not used in the second mode (this rule is switched off) such that a dose increase cannot be suggested.

Further, if at least C FBG values for last D days is less than a FBG target lower limit, the intermediary result is determined as the preceding medicament dose value decreased by the greater of Z1 units or Z2% of the preceding medicament dose value (for example C=7, D=20, Z1=2, Z2=5). The suggestion for a subsequent medicament dose value may be determined as being the intermediary result or the arithmetic mean of the upper dose limit value and the intermediary result.

The calculated suggestion for a subsequent medicament dose value is then displayed at the display 162. There may be provided the possibility that the proposed insulin dose is confirmed and saved in case the user immediately administers the suggested dose. In this case the suggested and administered dose is saved in storage unit 130. Alternatively, the user may change the suggested dose and save it after administration.

When the medical device 100 is in the "Titration" route, the device may turn into the sleep state automatically after for example 120 seconds without any new action.

Finally, it is pointed out that device 100 may be realized as a two-part device, wherein the data storage 130, the receiving unit 120, the processor 140, the user input unit 150, the display unit 160, the interface unit 170, and the clock unit 180 are realized in a device like a smartphone or another computer separate from the measurement unit 110. The inventive method runs as a software program (application or "app") on the hardware of the device. The keys 151, 152, 153 and 154 are realized in this case as button fields on the display of a touchscreen.

The invention claimed is:

1. A blood glucose meter comprising:
    a blood glucose measurement unit configured to generate a plurality of measurement values of a fasting blood glucose level;
    a data storage configured to store:
        the plurality of measurement values of the fasting blood glucose level generated by the blood glucose measurement unit,
        a plurality of medicament dose values of a basal insulin or an insulin analogue applied before the plurality of measurement values are generated,
        time information associated with the plurality of measurement values comprising one or more times at which the plurality of measurement values are generated by the blood glucose measurement unit,
        time information associated with the plurality of medicament dose values comprising one or more times at which the plurality of medicament dose values are applied, and
        a target range of the fasting blood glucose level for titration of the basal insulin or the insulin analogue, wherein the target range comprises a lower limit and an upper limit; and
    a processor operatively coupled to the data storage and the blood glucose measurement unit, the processor being configured to execute a plurality of instances of a titration route comprising a first mode and a second mode and to provide a suggestion to a user for a subsequent medicament dose value of the basal insulin or the insulin analogue in the first mode of the titration route or in the second mode of the titration route, wherein at an initial instance of the plurality of instances of the titration route, the titration route is in the first mode, wherein the processor is configured to, for each respective instance of the plurality of instances:

in the first mode of the titration route,
check a first condition using the time information associated with the plurality of measurement values, wherein the processor is configured to determine that the first condition is true if the plurality of measurement values is below the upper limit of the target range (i) over a predetermined period of time or (ii) for a predetermined number of measurement values, wherein the predetermined number of measurement values correspond to measurement values of the plurality of measurement values within the predetermined period of time generated before the respective instance of the plurality of instances of the titration route, if the first condition is true, switch from the first mode to the second mode, and if the first condition is not true, determine the suggestion for the subsequent medicament dose value based on at least one first predefined calculation rule using at least one measurement value of the fasting blood glucose level and a medicament dose value, wherein the medicament dose value corresponds to (i) a last one of the plurality of medicament dose values applied before the respective instance of the plurality of instances of the titration route, (ii) a mean value of a predefined number of last ones of the plurality of medicament dose values applied before the respective instance of the plurality of instances of the titration route, or (iii) a mean value of medicament dose values of the plurality of medicament dose values applied over a predefined time period before the respective instance of the plurality of instances of the titration route, and in the second mode of the titration route, execute a second predefined calculation rule to
determine an intermediary result based on the at least one first predefined calculation rule using the at least one measurement value of the fasting blood glucose level and the medicament dose value,
compare the intermediary result with a dose limit value,
if the intermediary result is greater than or equal to the dose limit value, determine the suggestion for the subsequent medicament dose value to be the dose limit value, and
if the intermediary result is not greater than or equal to the dose limit value, determine the suggestion for the subsequent medicament dose value to be (i) the intermediary result or (ii) a value between the intermediary result and the dose limit value calculated by a third calculation rule, the value corresponding to an arithmetic mean of the intermediary result and the dose limit value.

2. The blood glucose meter according to claim 1, wherein the processor is further configured to determine the suggestion for the subsequent medicament dose value by the at least one first predefined calculation rule and additionally based on information about a physiological parameter or an event with regard to the user, the physiological parameter being distinct from the fasting blood glucose level.

3. The blood glucose meter according to claim 1, wherein the processor is further configured to, for each respective instance of the plurality of instances, receive a data input related to the fasting blood glucose level, wherein the data input comprises at least one of the following physiological parameters:

an occurrence or a number of hypoglycemic events after a first predetermined point in time, wherein the first predetermined point in time corresponds to (i) time information associated with a last use of the blood glucose meter by the user before the respective instance of the plurality of instances of the titration route, (ii) time information associated with a last one of the plurality of measurement values, or (iii) time information associated with the last one of the plurality of medicament dose values, or an occurrence or a number of hyperglycemic events after a second predetermined point in time, wherein the second predetermined point in time corresponds to (i) the time information associated with the last use of the blood glucose meter by the user before the respective instance of the plurality of instances of the titration route, (ii) the time information associated with the last one of the plurality of measurement values, or (iii) the time information associated with the last one of the plurality of medicament dose values.

4. The blood glucose meter according to claim 1, wherein the at least one first predefined calculation rule comprises the following steps:

if the plurality of measurement values include at least a first predetermined number of measurement values generated within a first predetermined number of days before the respective instance of the plurality of instances of the titration route and if a median of the at least the first predetermined number of measurement values of the fasting blood glucose level for the first predetermined number of days is above the upper limit of the target range, then increasing the medicament dose value by a first predetermined number of units every second predetermined number of days; and if the plurality of measurement values include at least a second predetermined number of measurement values generated within a third predetermined number of days before the respective instance of the plurality of instances of the titration route are less than the lower limit of the target range, then decreasing the medicament dose value by a greater one of a second predetermined number of units or a percentage of the last one of the plurality of medicament dose values.

5. A method performed by a blood glucose meter, the blood glucose meter comprising
a blood glucose measurement unit configured to generate a plurality of measurement values of a fasting blood glucose level,
a data storage configured to store
the plurality of measurement values of the fasting blood glucose level generated by the blood glucose measurement unit,
a plurality of medicament dose values of a basal insulin or an insulin analogue applied before the plurality of measurement values are generated,
time information associated with the plurality of measurement values comprising one or more times at which the plurality of measurement values are generated by the blood glucose measurement unit, time information associated with the plurality of medicament dose values comprising one or more times at which the plurality of medicament dose values are applied, and a target range of the fasting blood glucose level for titration of the basal insulin or the insulin analogue, wherein the target range comprises a lower limit and an upper limit, and a processor operatively coupled to the data storage and the blood glucose measurement unit, the method comprising:

(i) executing, by the processor of the blood glucose meter, a plurality of instances of a titration route comprising a first mode and a second mode, wherein executing the plurality of instances of the titration route comprises executing an initial instance of the plurality of instances of the titration route in the first mode;

(ii) providing, by the processor of the blood glucose meter in the titration route, a suggestion for a subsequent medicament dose value of the basal insulin or the insulin analogue in the first mode or in the second mode of the titration route; and (iii) for each respective instance of the plurality of instances:

in the first mode of the titration route:
checking, by the processor, a first condition using the time information associated with the plurality of measurement values, wherein checking the first condition comprises determining that the first condition is true if the plurality of measurement values is below the upper limit of the target range (i) over a predetermined period of time or (ii) for a predetermined number of measurement values, wherein the predetermined number of measurement values correspond to measurement values of the plurality of measurement values within the predetermined period of time generated before the respective instance of the plurality of instances of the titration route, if the first condition is true, switching, by the processor, the titration route from the first mode to the second mode, and if the first condition is not true, determining, by the processor, the suggestion for the subsequent medicament dose value based on at least one first predefined calculation rule using at least one measurement value of the fasting blood glucose level and a medicament dose value, wherein the medicament dose value corresponds to (i) a last one of the plurality of medicament dose values applied before the respective instance of the plurality of instances of the titration route, (ii) a mean value of a predefined number of last ones of the plurality of medicament dose values applied before the respective instance of the plurality of instances of the titration route, or (iii) a mean value of medicament dose values of the plurality of medicament dose values applied over a predefined time period before the respective instance of the plurality of instances of the titration route; and in the second mode of the titration route, executing, by the processor, a second predefined calculation rule by:

determining an intermediary result based on the at least one first predefined calculation rule using the at least one measurement value of the fasting blood glucose level and the medicament dose value, comparing the intermediary result with a dose limit value, if the intermediary result is greater than or equal to the dose limit value, determining the suggestion for the subsequent medicament dose value to be the dose limit value, and if the intermediary result is not greater than or equal to the dose limit value, determining the suggestion for the subsequent medicament dose value to be (i) the intermediary result or (ii) a value between the intermediary result and the dose limit value calculated by a third calculation rule, the value corresponding to an arithmetic mean of the intermediary result and the dose limit value.

6. The method according to claim 5, further comprising, for each respective instance of the plurality of instances, receiving a data input related to the fasting blood glucose level, wherein the data input comprises at least one of the following physiological parameters:

an occurrence or a number of hypoglycemic events after a first predetermined point in time, wherein the first predetermined point in time corresponds to (i) time information associated with a last use of the blood glucose meter by a user before the respective instance of the plurality of instances of the titration route, (ii) time information associated with a last one of the plurality of measurement values, (iii) time information associated with the last one of the plurality of medicament dose values, or an occurrence or a number of hyperglycemic events after a second predetermined point in time, wherein the second predetermined point in time corresponds to (i) the time information associated with the last use of the blood glucose meter by the user before the respective instance of the plurality of instances of the titration route, (ii) the time information associated with the last one of the plurality of measurement values, or (iii) the time information associated with the last one of the plurality of medicament dose values.

7. The method according to claim 5, wherein the at least one first predefined calculation rule comprises the following steps:

if the plurality of measurement values include at least a first predetermined number of measurement values generated within a first predetermined number of days before the respective instance of the plurality of instances of the titration route and if a median of the at least the first predetermined number of measurement values of the fasting blood glucose level for the first predetermined number of days is above the upper limit of the target range, then increasing the medicament dose value by a first predetermined number of units every second predetermined number of days; and if the plurality of measurement values include at least a second predetermined number of measurement values generated within a third predetermined number of days before the respective instance of the plurality of instances of the titration route are less than the lower limit of the target range, then decreasing the medicament dose value by a greater one of a second predetermined number of units or a percentage of the last one of the plurality of medicament dose values.

8. The method according to claim 5, wherein providing the suggestion for the subsequent medicament dose value comprises providing the suggestion for the subsequent medicament dose value by the at least one first predefined calculation rule and additionally based on information about a physiological parameter or an event with regard to a user, the physiological parameter being distinct from the fasting blood glucose level.

9. A non-transitory computer readable medium storing instructions for operating a blood glucose meter, the blood glucose meter comprising
  a blood glucose measurement unit configured to generate a plurality of measurement values of a fasting blood glucose level,
  a data storage configured to store:
    the plurality of measurement values of the fasting blood glucose level generated by the blood glucose measurement unit,
    a plurality of medicament dose values of a basal insulin or an insulin analogue applied before the plurality of measurement values are generated,
    time information associated with the plurality of measurement values comprising one or more times at which the plurality of measurement values are generated by the blood glucose measurement unit,
    time information associated with the plurality of medicament dose values comprising one or more times at which the plurality of medicament dose values are applied, and
    a target range of the fasting blood glucose level for titration of the basal insulin or the insulin analogue, wherein the target range comprises a lower limit and an upper limit, and
  a processor operatively coupled to the data storage and the blood glucose measurement unit,
  wherein the instructions are executable by the processor to perform operations comprising:
    (i) executing, by the processor of the blood glucose meter, a plurality of instances of a titration route comprising a first mode and a second mode, wherein executing the plurality of instances of the titration route comprises executing an initial instance of the plurality of instances of the titration route in the first mode;
    (ii) determining, by the processor in the titration route, a suggestion for a subsequent medicament dose value of the basal insulin or the insulin analogue in the first mode or in the second mode of the titration route; and
    (iii) for each respective instance of the plurality of instances of the titration route:
      in the first mode of the titration route:
        checking, by the processor, a first condition using the time information of the plurality of measurement values, wherein checking the first condition comprises determining that the first condition is true if the plurality of measurement values is below the upper limit of the target range (i) over a predetermined period of time or (ii) for a predetermined number of measurement values, wherein the predetermined number of measurement values correspond to measurement values of the plurality of measurement values within the predetermined period of time before the respective instance of the plurality of instances of the titration route,
        if the first condition is true, switching, by the processor, the titration route from the first mode to the second mode, and
        if the first condition is not true, determining, by the processor, the suggestion for the subsequent medicament dose value based on at least one first predefined calculation rule using at least one measurement value of the fasting blood glucose level and a medicament dose value, wherein the medicament dose value corresponds to (i) a last one of the plurality of medicament dose values applied before the respective instance of the plurality of instances of the titration route, (ii) a mean value of a predefined number of last ones of the plurality of medicament dose values applied before the respective instance of the plurality of instances of the titration route, or (iii) a mean value of medicament dose values of the plurality of medicament dose values applied over a predefined time period before the respective instance of the plurality of instances of the titration route; and
      in the second mode of the titration route, executing, by the processor, a second predefined calculation rule by:
        determining an intermediary result based on the at least one first predefined calculation rule using the at least one measurement value of the fasting blood glucose level and the medicament dose value,
        comparing the intermediary result with a dose limit value,
        if the intermediary result is greater than or equal to the dose limit value, determining the suggestion for the subsequent medicament dose value to be the dose limit value, and
        if the intermediary result is not greater than or equal to the dose limit value, determining the suggestion for the subsequent medicament dose value to be (i) the intermediary result or (ii) a value between the intermediary result and the dose limit value calculated by a third calculation rule, the value corresponding to an arithmetic mean of the intermediary result and the dose limit value.

10. The non-transitory computer readable medium according to claim 9, wherein the at least one first predefined calculation rule comprises the following steps:
  if the plurality of measurement values include at least a first predetermined number of measurement values generated within a first predetermined number of days before the respective instance of the plurality of instances of the titration route and if a median of the at least the first predetermined number of measurement values of the fasting blood glucose level for the first predetermined number of days is above the upper limit of the target range, then increasing the medicament dose value by a first predetermined number of units every second predetermined number of days; and
  if the plurality of measurement values include at least a second predetermined number of measurement values generated within a third predetermined number of days before the respective instance of the plurality of instances of the titration route are less than the lower limit of the target range, then decreasing the medicament dose value by a greater one of a second predetermined number of units or a percentage of the last one of the plurality of medicament dose values.

11. The non-transitory computer readable medium according to claim 9, wherein providing the suggestion for the subsequent medicament dose value comprises providing the suggestion for the subsequent medicament dose value by the at least one first predefined calculation rule and additionally based on information about a physiological parameter or an event with regard to a user, the physiological parameter being distinct from the fasting blood glucose level.

12. The non-transitory computer readable medium according to claim 9, wherein the operations further comprise receiving a data input related to the fasting blood glucose level, wherein the data input comprises at least one of the following physiological parameters:

an occurrence or a number of hypoglycemic events after a first predetermined point in time, wherein the first predetermined point in time corresponds to (i) time information associated with a last use of the blood glucose meter by a user before the respective instance of the plurality of instances of the titration route, (ii) time information associated with a last one of the plurality of measurement values, or (iii) time information associated with the last one of the plurality of medicament dose values, or an occurrence or a number of hyperglycemic events after a second predetermined point in time, wherein the second predetermined point in time corresponds to (i) the time information associated with the last use of the blood glucose meter by the user before the respective instance of the plurality of instances of the titration route, (ii) the time information associated with the last one of the plurality of measurement values, or (iii) the time information associated with the last one of the plurality of medicament dose values.

* * * * *

UNITED STATES PATENT AND TRADEMARK OFFICE
CERTIFICATE OF CORRECTION

PATENT NO. : 11,017,891 B2  
APPLICATION NO. : 15/324997  
DATED : May 25, 2021  
INVENTOR(S) : Andrew Tubb Page 1 of 1

It is certified that error appears in the above-identified patent and that said Letters Patent is hereby corrected as shown below:

In the Claims

In Column 20, Line 30, Claim 6, after "values," insert -- or --

Signed and Sealed this  
Twenty-sixth Day of October, 2021

Drew Hirshfeld  
*Performing the Functions and Duties of the*  
*Under Secretary of Commerce for Intellectual Property and*  
*Director of the United States Patent and Trademark Office*